United States Patent
Mullins et al.

(10) Patent No.: US 11,268,888 B1
(45) Date of Patent: Mar. 8, 2022

(54) SYSTEMS AND METHODS FOR DETERMINING CONCRETE STRENGTH

(71) Applicant: UNIVERSITY OF SOUTH FLORIDA, Tampa, FL (US)

(72) Inventors: Austin Gray Mullins, Bradenton, FL (US); Sarah Jo Mobley, Tampa, FL (US); Kelly Marie Costello, Boca Raton, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 242 days.

(21) Appl. No.: 16/226,593

(22) Filed: Dec. 19, 2018

Related U.S. Application Data

(60) Provisional application No. 62/607,559, filed on Dec. 19, 2017.

(51) Int. Cl.
*G01N 3/00* (2006.01)
*G01N 3/10* (2006.01)
*G01N 33/38* (2006.01)

(52) U.S. Cl.
CPC ............. *G01N 3/10* (2013.01); *G01N 33/383* (2013.01); *G01N 2203/0019* (2013.01); *G01N 2203/0044* (2013.01); *G01N 2203/0676* (2013.01); *G01N 2203/0682* (2013.01)

(58) Field of Classification Search
None
See application file for complete search history.

(56) References Cited

U.S. PATENT DOCUMENTS

| | | |
|---|---|---|
| 3,557,886 A | 1/1971 | Cobbs |
| 3,974,679 A | 8/1976 | Nasser |
| 7,181,978 B2 | 2/2007 | Shtakelberg |
| 7,289,916 B2 | 10/2007 | Drnevich |
| 8,794,078 B2 | 8/2014 | Darbe |
| 2015/0233806 A1* | 8/2015 | More ................. G01N 3/40 73/85 |
| 2017/0059385 A1* | 3/2017 | Vander Horst ..... G01F 23/0046 |
| 2018/0128724 A1* | 5/2018 | Pinillos ................. G01N 19/04 |

FOREIGN PATENT DOCUMENTS

| | | | | |
|---|---|---|---|---|
| EP | 2573557 A1 * | 3/2013 | ........... | G01N 33/383 |
| JP | 59137839 A * | 8/1984 | ............... | G01N 3/00 |

(Continued)

OTHER PUBLICATIONS

Product by STIHL called "Pressurized Water Tank" with description available at https://www.stihlusa.com/products/cut-off-machines/cut-off-machine-accessories/presstank/ and sold at least by at least in 2015. (Year: 2015).*

(Continued)

*Primary Examiner* — Blake A Tankersley

(57) ABSTRACT

In one embodiment, a concrete strength testing system includes a core drill having a core barrel, a press associated with the core drill that is configured to drive the core barrel into concrete to be tested, a force sensor associated with the core drill that is configured to measure a force with which the core barrel is driven into the concrete by the press, and a depth measurement device configured to measure a depth into the concrete to which the core barrel is driven by the press.

8 Claims, 4 Drawing Sheets

(56) References Cited

FOREIGN PATENT DOCUMENTS

JP          2008128831 A  *  6/2008  ........... G01N 33/383
JP          2015212637 A  *  11/2015

OTHER PUBLICATIONS

Wayback Machine screen capture of article titled "Power Triangle and Power Factor" on Electronic Tutorials captured on Aug. 12, 2016 and available at https://web.archive.org/web/20160812060346/https://www.electronics-tutorials.ws/accircuits/power-triangle.hlml (Year: 2016).*
Yamamoto, et al., "Evaluation of compressive strength of concrete using small diameter core" Third international conference on sustainable construction materials and technologies; Aug. 2013.
Beckhaus, K, EFFC/DFI Best practice guide to tremie concrete for deep foundations (1st ed); Hawthorne, NJ; Deep Foundations Institute, 2016.
Brown, D., "Recipe for sucess with drilled shaft concrete", Foundation Drilling Magazine, 16-24, 2004.
Brown, D.A., et al. Drilled shafts: construction procedures and LRFD design methods., McLean, VA; US Dept of Transportion, Federal Highway Administration, 2010.
Costello, K., et al., "Evaluation of self consolidating concrete and class IV concrete flow in drilled shafts part 1", FDOT project No. BDKV25-TW0977-25, Chapter 3, 2017.
Mullins, et al., "Defining the Upper Viscosity Limit for Mineral Slurries Used in Drilled Shaft Construction", FDOT project BDK84-977-24, final report, 2014.
Deese, et al., "Factors affecting concrete flow in drilled shaft construction," ADSC DE03, FEO Construction quality assurance / quality control conference proceedings, Nov. 2005.

\* cited by examiner

SYSTEMS AND METHODS FOR DETERMINING CONCRETE STRENGTH

CROSS-REFERENCE TO RELATED APPLICATION

This application claims priority to U.S. Provisional Application Ser. No. 62/607,559, filed Dec. 19, 2017, which is hereby incorporated by reference herein in its entirety.

BACKGROUND

Concrete is a preferred construction material for many civil engineering structures due to its strength, cost-effectiveness, and durability. Concrete typically comprises cement, sand, crushed rock aggregates, and water. Variants of cementing materials and aggregates can be used to increase performance. Most often, concrete is delivered to a project site as a viscous fluid in large trucks and poured into forms that may be above or below ground. Regardless of the application, concrete is designed to have a specified strength. Unfortunately, concrete, and its properties, can be inadvertently altered by various on-site factors. These factors can include one or more of temperature, extended drive times or construction delays, improper mix proportions, unintended use of admixtures, incomplete/poor mixing, segregation or mixing with ground water, or attack from chemical agents in the soil or environment.

Given that such on-site factors can adversely affect the strength of concrete, it is common practice to test the liquid concrete, and the cured concrete formed from it, onsite. This normally involves verifying the fluidity upon arrival, noting the amount of mixing the entire truck drum has imparted into that batch, and preparing cylindrical specimens that harden on-site and are then periodically tested for compressive strength to confirm strength gain. Even with these safeguards, situations arise where the quality of the as-placed concrete comes into question. In these events, the most robust assurance mechanism is to take a core sample of the curing concrete and test the compressive strength. The sample size is often similar to the cylinders prepared for quality assurance when the truck arrived on-site (e.g., 4 inches in diameter). Standard specifications require that the compression test sample be twice as long as the diameter, meaning that only one data point can be obtained for every 8 inches of core concrete length. Additionally, the process requires that the full-length cores be cut to the proper length with squared ends and then tested in compression.

The above-described testing process is time-consuming and only provides a discrete number of samples, which is further reduced by breaks in the recovered samples, making portions of the core unusable. It can therefore be appreciated that it would be desirable to have alternative systems and methods for determining the strength of the in-place concrete.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have alternative systems and methods for determining the strength of the concrete. Disclosed herein are examples of such systems and methods. In some embodiments, a concrete strength testing system comprises an instrumented core drill that is configured to instantaneously determine the equivalent compressive strength during drilling, thereby eliminating the need to perform compressive testing on collected cores. The drilled core hole can be much smaller (e.g., 1 inch in diameter) than the cores currently used in concrete strength testing, making the size of required equipment smaller and the influence of the coring on the structure less significant. A core sample is still retrieved, however, and can be used for verification or calibration.

In the following disclosure, various specific embodiments are described. It is to be understood that those embodiments are example implementations of the disclosed inventions and that alternative embodiments are possible. All such embodiments are intended to fall within the scope of this disclosure.

A goal of the disclosed inventions is to provide a system capable of generating and outputting a strength profile of concrete in real time. In concept, the system is a concrete penetrometer that measures the instantaneous concrete strength from concrete coring resistance via a fully instrumented concrete coring drill motor. Part of the novelty of the system is the simultaneous collection of data and the computational conversions to the in situ concrete strength profile. A significant advantage of use of the system is that it can reveal locally weak or strong portions of the concrete that may be missed from traditionally sized specimens.

Figure 1:
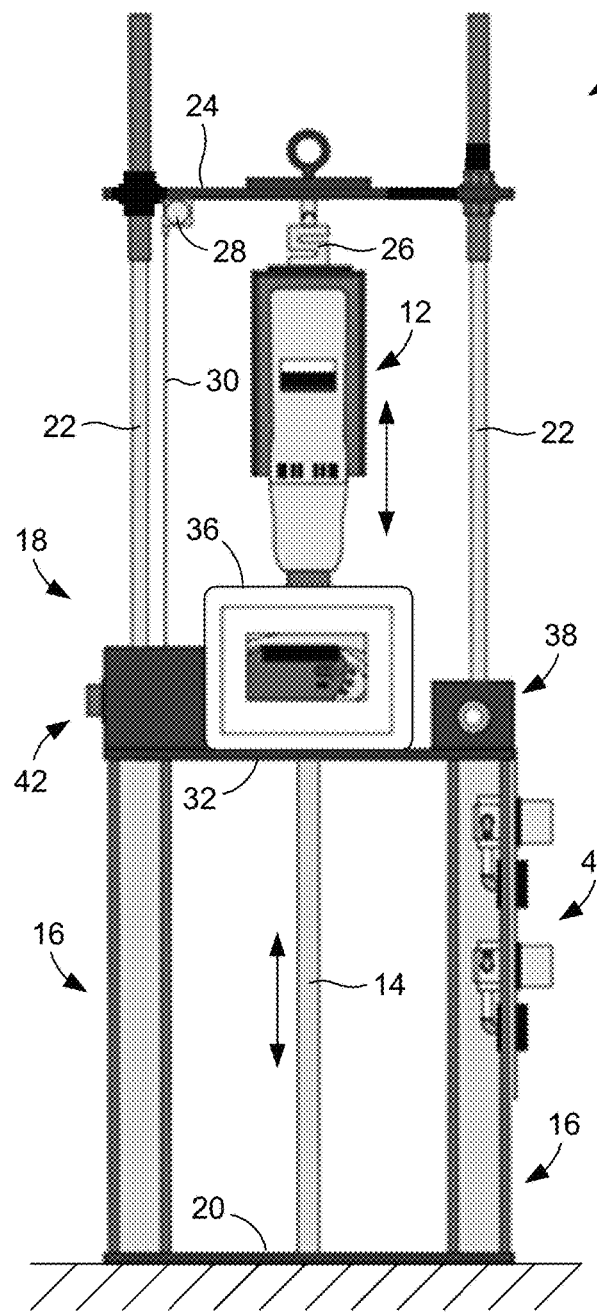
FIG. 1 is a front view of an embodiment of a concrete strength testing system.
Figure 2:
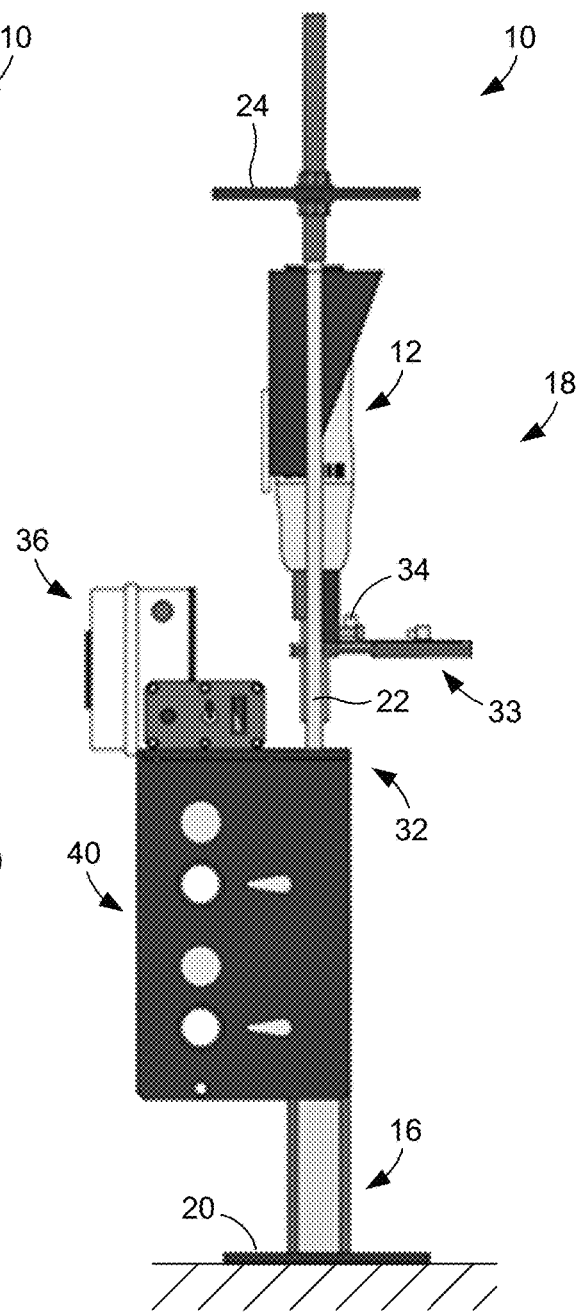
FIG. 2 is a side view of the system of FIG. 1.

FIGS. 1 and 2 illustrate an embodiment of a concrete strength testing system 10 configured to instantaneously determine concrete strength. As shown in the figures, the system 10 includes a core drill 12. The core drill 12 comprises an elongated core barrel 14 and can be raised and lowered using one or more presses 16, such as one or more pneumatic presses, which are mounted to a frame 18 that includes a base 20. In some embodiments, the core barrel 14 has a small diameter, such as approximately 1 in. In the illustrated embodiment, there are two presses 16 mounted to the base 20, one positioned on either side of the core drill 12. Extending upward from the presses 16 are elongated piston rods 22 that are connected to an upper cross-member 24 of the frame 18. As can be appreciated from FIG. 1, the core drill 12 is suspended from the upper cross-member 24. Positioned between the upper cross-member 24 and the core drill 12 is a force sensor 26, such as a load cell, configured to measure the force applied to the drill by the presses 16. Also suspended from the upper cross-member 24 is a depth measurement device 28. In some embodiments, the depth measurement device 28 comprises a string-line displacement transducer having a string 30 that is attached to a lower cross-member 32 of the frame 18. In such an embodiment, the depth measurement device 28 is configured to measure the distance between the upper cross-member 24 and the lower cross-member 32 and, therefore, the depth to which the core drill 12, and its core barrel 14, is driven into the concrete to be tested.

With further reference to FIGS. 1 and 2, the concrete strength testing system 10 also includes a rotational speed measurement device 33 that is configured to measure the speed with which the core barrel 14 rotates. In some embodiments, the rotational speed measurement device 33 comprises a rotary encoder that monitors revolutions of the core barrel 14. The system 10 further comprises a pressure sensor 34, such as a pressure transducer, configured to measure the pressure of fluid used to flush cuttings from the annulus around the core barrel 14. This pressure is useful to know as the fluid applies an upward (lifting) force on the core barrel 14 during drilling, in which case the force on the core drill 12 is actually the force applied by the press 16 minus the force applied by the fluid. In some embodiments, the system 10 further comprises a flow meter (not shown), such as a magnetic flux flow meter, which is configured to measure the flow rate of the fluid.

The concrete strength testing system 10 further includes a power meter 36 that is configured to measure the power (product of the current and voltage) drawn by the core drill 12. In other embodiments, the power meter 36 can be replaced or supplemented with a torque measurement device configured to measure the torque of the motor of the core drill 12. Such a measurement device can, for example, comprise one or more load cells that measure the force required to hold the core drill 12 against rotation as it is drilling the concrete or a torsional shear cell that is provided between the core drill and its core barrel 14.

Figure 3:
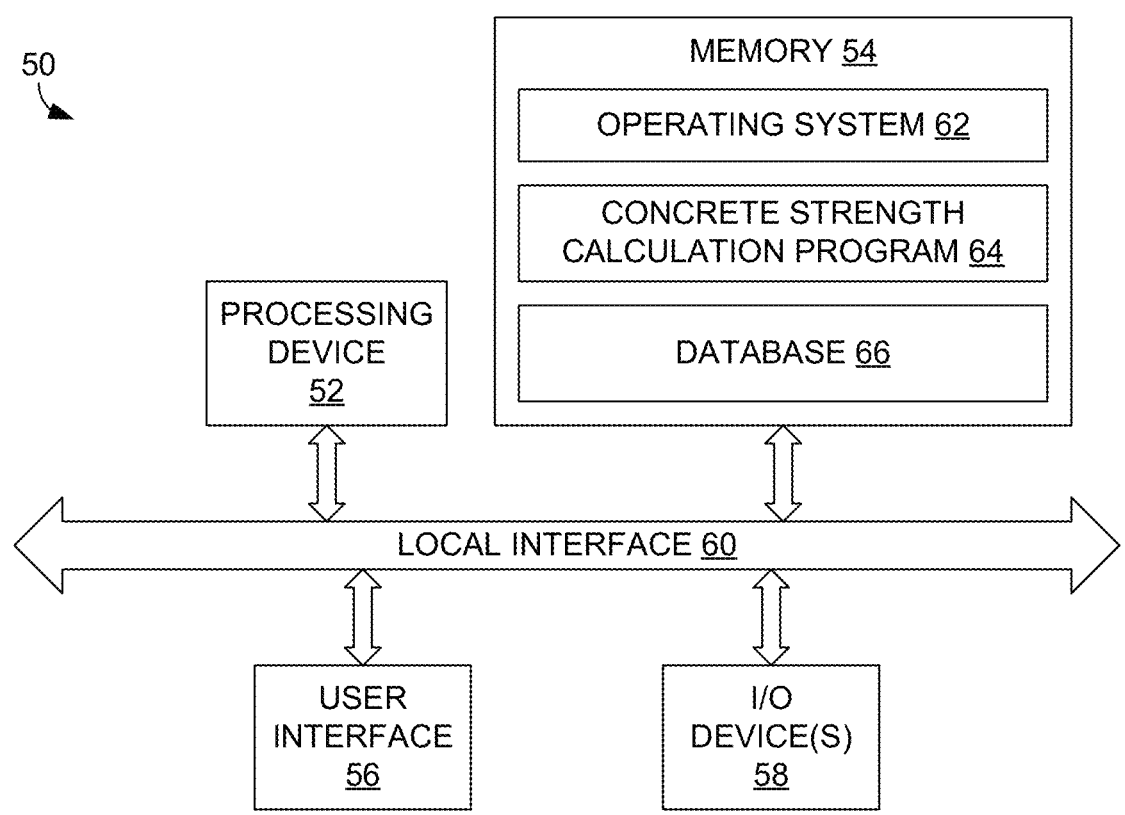
FIG. 3 is a block diagram of an embodiment of a computing device that can calculate concrete strength based upon data collected by the system of FIGS. 1 and 2.

In addition to the aforementioned components, the concrete strength testing system 10 further includes a power supply 38 (e.g., battery) that provides power to the system, a control panel 40 that can be used by a user to operate the system, as well as a communication port 42 that can be used to export data collected by the system to another system, such as a desk or notebook computing device (see, e.g., FIG. 3).

A prototype system similar to that described above was developed and evaluated. The platform of the prototype system was a Milwaukee 4049, 20-amp manually-operated coring machine fitted with a 1-inch inner diameter, diamond-tip core barrel. This is a wet core drill that lowers and lifts the core barrel with a linear gear, rack-and-pinion configuration, wherein turning the crank controls crowd and advances or retracts the drill with a manually-applied, variable force.

Producing usable and replicable data for instantaneous strength determination necessitated the isolation of variables that affect core drilling effectiveness including: downward force on core barrel (crowd), rotational speed, torque, advancement rate, power consumption, fluid flow, and fluid pressure. Mechanically, the linear gear/crank assembly was removed and replaced with two Parker 4MA series, 24-inch stroke, 2.5-inch diameter, double-acting pneumatic cylinders. These pneumatic cylinders enable complete user control of the force applied by a pneumatic press by using two air pressure regulators each that independently controlled the downward crowd or upward extraction force. The exact force applied to the drill motor and core barrel was monitored using an Omega LCCD-2K, 2000-pound capacity load cell connected between the pneumatic cylinder and the core drill motor.

A Celesco SP2-50 string-line displacement transducer with a 50-inch range was used to record the depth of coring. By recording the associated coring time, the vertical advancement rate could also be determined. The rotational speed (rpm) was measured with a BEI, H20 incremental rotary encoder mounted to a 2:1 ratio set of pulse wheels. Because fluid was also used to flush cuttings from the annulus around the core barrel and, in turn, affects drilling performance, the pressure of the fluid was monitored with Honeywell Model AB/HP 6 psi pressure transducer.

The variation in power that resulted from additional crowd and drilling resistance was directly monitored using a GE PQMII power quality meter. This meter combines voltage with current taken using an Omega RCT151205A current coil to produce a power output that takes into account the effects of phase shift. All data was monitored and recorded using a Model BMS16HR-53 Titan Mini-recorder computerized data acquisition unit from Mars Labs. The data sampling rate was 128 Hz.

The result of this instrumentation was a drilling machine with the ability to provide dynamic force, velocity, pressure, power, and rotational speed. In post-processing, this data could then be used to determine the resistive force and strength of the concrete. This data analysis process is described below.

Preliminary verification tests were conducted using the system where each of the transducer outputs was checked.

Rotational Speed

Rotational speed can serve as a quality control check for the final calculations based on the idea that, given a constant applied drilling force, the rate of rotation should increase or decrease with corresponding changes in concrete strength. Rotation was calibrated through use of the totalizer option on the data acquisition unit. The core barrel was turned manually and the rotations tallied, this result was then compared to the total rotations recorded. Good agreement was noted.

Power

In lieu of measuring torque and multiply it by rpm to compute power, the electrical power meter was implemented that simultaneously measures the current, voltage, and phase angle. The importance lies in the phase angle measurement that was not previously measured and where the actual power draw is the product of voltage, current, and the cosine of the phase angle. Previous measurements assumed a phase angle to be small and where the power factor (cosine of the phase angle) was taken as a constant of 0.9 based on spot checked values. The new power meter is thought to be a significant advantage by removing this assumption.

Displacement

While somewhat trivial compared to the other transducers, the string-line transducer was confirmed to register the full 18 in. stroke of the pneumatic cylinder. Like rotational speed, the advancement rate was then computed using the timestamps associated with each data point.

Pressure

Pressure of the drilling fluid, if appreciable, could reduce the net force on the cutting edge of the core barrel. However, the anticipated pressure range was small and the 6-psi transducer range made simple calibration checks possible by using a simple column of water and comparing the hydrostatic pressure with that registered. Good agreement was noted.

Testing Procedure

The process of coring was standardized to provide baseline measurements of crowd, displacement, rpm, and power prior to making contact with the concrete surface. The base plate of the core rig was equipped with slots to allow for the installation of a mechanical rebar splice as a means to secure the machine to the shaft surface. The testing procedure was performed as follows:
1. Set data acquisition unit to scan.
2. Balance transducers.
3. Turn on water.
4. Power core drill.
5. Wait 5 seconds.
6. Begin recording data.
7. Wait 3 seconds.
8. Slowly turn the vent knob from the "OFF" to the "DRILL" position allowing the core barrel to come in contact with the concrete surface gently.
9. Turn the Pressure knob from the "OFF" to the "DRILL" position.
10. Monitor transducer readings during drilling operations.
11. Once drilling operations are complete allow the drill to run for an additional 3 seconds.
12. Turn off power.
13. Stop recording data.
14. Carefully extract core barrel and check for any concrete prior to setting up at the next drilling location.

Results

The system was instrumented to provide all necessary information used to calculate the specific energy. This, in turn, is correlated to the strength of rock or cemented materials during rotary, non-percussive drilling operations. Therein, crowd, rotational speed, torque, and displacement measurements are required (Equation (1)):

$$e = \frac{F}{A} + \frac{2\pi}{A}\left(\frac{NT}{u}\right) \quad (1)$$

wherein:
e=specific energy (psi)
F=crowd (lbs)
A=core bit area (in$^2$)
N=rotational speed (rev/min)
T=torque (lb-in)
u=penetration rRate (in/min)

The concrete penetrometer used the same equation but where power, P, was measured directly (Equation 2):

$$P = TN2\pi \quad (2)$$

By combining Equations (1) and (2), Teale's expression simplifies into Equation (3):

$$e = \frac{F}{A} + \frac{P}{Au} \quad (3)$$

The specific energy is then equated to compressive strength (f'c) using an empirical relationship (Equation 4) where the coefficients a and b are both a function of the penetration rate:

$$f'c = \frac{b + \sqrt{(b^2 - 4ae)}}{2a} \quad (4)$$

wherein f'c=compressive strength (psi).

The strength is then averaged per 1/16" and graphed against depth. Notably, all of the above calculations can be automatically performed by a computing device that receives the data collected by the data acquisition unit. FIG. 3 shows an example configuration of such a computing device. The computing device 50 generally comprises a processing device 52, memory 54, a user interface 56, and one or more input/output (I/O) devices 58, each of which is connected to a system bus 60. The processing device 52 can, for example, include a central processing unit (CPU) that is capable of executing computer-executable instructions stored within the memory 54. The memory 54 can include any one of or a combination of volatile memory elements (e.g., RAM, flash, etc.) and nonvolatile memory elements (e.g., hard disk, ROM, etc.). The user interface 56 can comprise one or more devices that can enter user inputs into the computing device 50, such as a keyboard and mouse, as well as one or more devices that can convey information to the user, such as a display. The I/O devices 68 can comprise components that enable the computing device 50 to communicate with other devices, such as a network adapter.

The memory 54 (a non-transitory computer-readable medium) stores software applications (programs) including an operating system 62 and a concrete strength calculation program 64 configured to calculate concrete strength and, optionally, graph the results. The concrete strength calculation program 74 includes computer-executable instructions, which may be comprised by one or more algorithms (i.e., computer logic), which can be executed by the processing device 52. Results computed by the program 74 can optionally be stored in a database 66.

Figure 4:
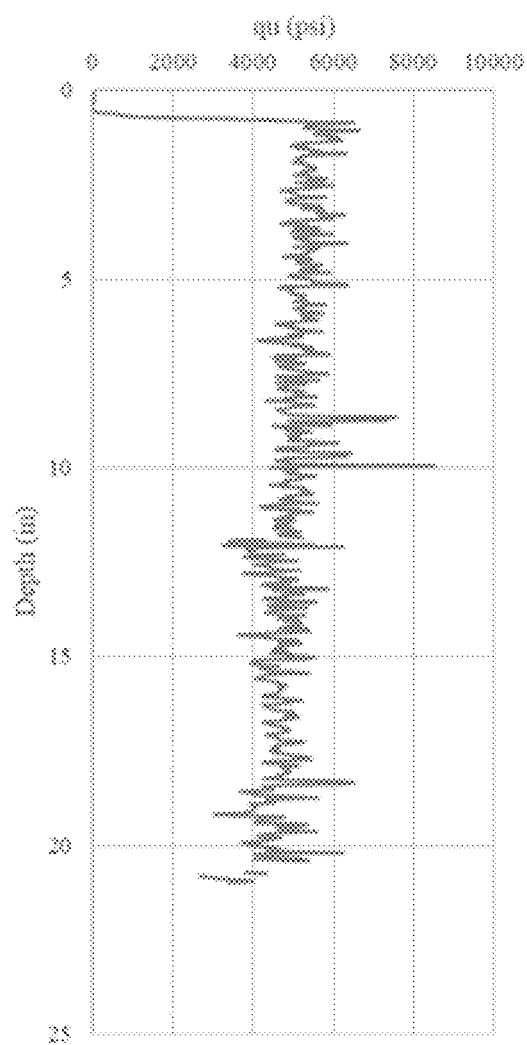
FIG. 4 is a graph that plots core strength (strength vs. depth) for a test specimen tested using a prototype concrete strength testing system similar to that illustrated in FIGS. 1 and 2.
Figure 5:
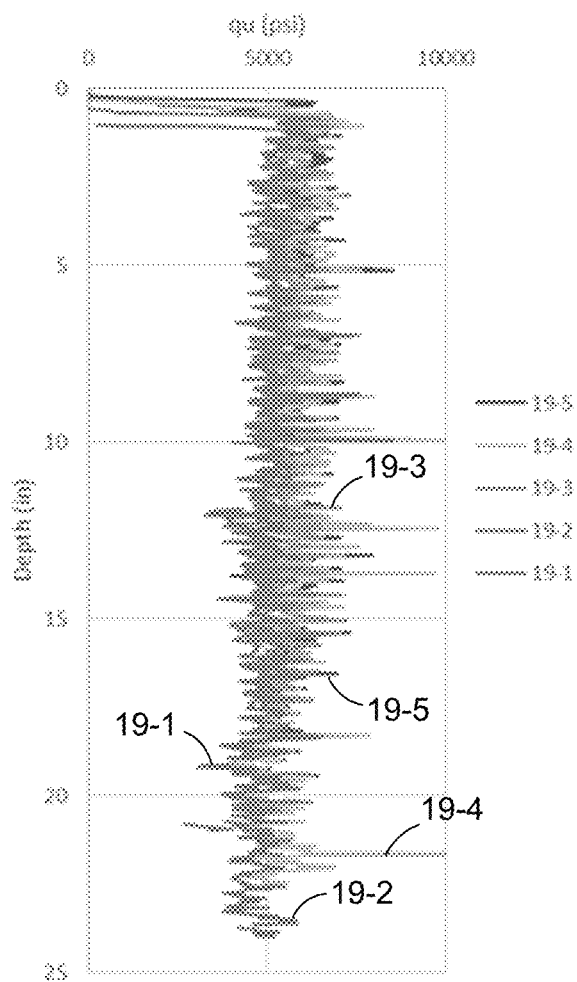
FIG. 5 is a graph that plots core strength (strength vs. depth) for multiple test specimens tested using a prototype concrete strength testing system similar to that illustrated in FIGS. 1 and 2.

FIG. 4 shows the results from a sample coring. FIG. 5 shows the results of several cores taken on a single shaft. The variation in average strength is consistent with the calculated strength in disparate regions on the specimen.

This device was used to test concrete samples too small to show trends that were needed to demonstrate whether or not concrete was being compromised by submerged casting environments. Without the novel device, strength variation throughout the concrete specimens could not have been determined. To date, 35 of the 58 test specimens have been cored in a similar manner. In order to analyze the effect of slurry on concrete in the cover region, the average strength was determined for each core. The strengths associated with the cores in the annular cover region were then compared to the average interior strength, which was used as a baseline for each shaft. These results are grouped by casting environment (slurry type) and shown in Tables 1-3 below.

TABLE 1

Strength ratios - Bentonite

Bentonite

| Shaft # | Viscosity (sec) | Baseline Strength (psi) | Ratio To Crease | Ratio To Cover 1 | Ratio To Cover 2 |
|---|---|---|---|---|---|
| 9 | 57 | 5136.75 | 0.81 | 0.74 | 0.96 |
| 10 | 90 | 4654.67 | 0.85 | 0.84 | 0.88 |
| 15 | 56 | 4712.35 | 1.05 | 1.05 | 1.12 |
| | | | | Average | 0.92 |

TABLE 2

Strength ratios - Polymer
Polymer

| Shaft # | Viscosity (sec) | Baseline Strength (psi) | Ratio To Crease | Ratio To Cover 1 | Ratio To Cover 2 |
|---|---|---|---|---|---|
| 11 | 65 | 4180.95 | 1.05 | 1.24 | 1.07 |
| 17 | 85 | 4345.25 | 0.91 | 0.91 | 0.93 |
| 19 | 63 | 5736.00 | 0.84 | 0.86 | 0.97 |
|  |  |  |  | Average | 0.98 |

TABLE 3

Strength ratios - water
Water

| Shaft # | Viscosity (sec) | Baseline Strength (psi) | Ratio To Crease | Ratio To Cover 1 | Ratio To Cover 2 |
|---|---|---|---|---|---|
| 6 | 26 | 4383.24 | 0.92 | 0.95 | 0.93 |

When looking at the loss of strength between the interior and cover region cores, the bentonite cast shafts show the largest reduction with an average ratio of 0.92. The largest individual loss of 0.74 was also in a bentonite cast shaft. The polymer cast shafts stayed fairly consistent as did the water. Again, previous methods of testing these specimens would have resulted in only 6 data points (3 inside the cage and 3 outside the cage). The new device/method was able to full discriminate along the full core length.

The invention claimed is:

1. A method for testing concrete strength, the method comprising:
   drilling into concrete to be tested with a core drill;
   measuring a force with which a core barrel of the core drill is driven into the concrete;
   measuring a rotational speed of the core barrel;
   measuring a current, voltage, and phase angle of the core drill;
   measuring a pressure of fluid used to remove cuttings from around the core drill that are produced while drilling the concrete;
   measuring a depth to which the core barrel is driven into the concrete; and
   calculating the strength of the concrete based upon the measured force, rotational speed, current, voltage, phase angle, pressure, and depth.

2. The method of claim 1, wherein the drilling into the concrete comprises driving the core barrel into the concrete using a pneumatic press.

3. The method of claim 1, wherein the measuring of the force comprises measuring the force with a load cell associated with the core drill.

4. The method of claim 1, wherein the measuring of the depth comprises measuring the depth using a string-line displacement transducer.

5. The method of claim 1, wherein the measuring of the rotational speed of the core barrel comprises measuring the rotational speed using a rotary encoder.

6. The method of claim 1, wherein the measuring of the pressure of a fluid comprises measuring the pressure using a pressure transducer.

7. The method of claim 1, wherein the measuring of the current, voltage, and phase angle comprises measuring the current, voltage, and phase angle using a power meter.

8. The method of claim 1, wherein the calculating of the strength of the concrete comprises calculating the concrete strength using a computer configured to compute the concrete strength based upon the measured force, rotational speed, current, voltage, phase angle, pressure, and depth.

* * * * *